United States Patent [19]

Kaufman

[11] Patent Number: 4,923,700
[45] Date of Patent: May 8, 1990

[54] ARTIFICIAL TEAR SUSPENSION

[76] Inventor: Herbert E. Kaufman, 300 Lake Marina Dr., Unit 18E, New Orleans, La. 70124

[21] Appl. No.: 201,929
[22] Filed: Jun. 3, 1988
[51] Int. Cl.$^5$ ............................................ A61M 31/00
[52] U.S. Cl. .................................... 424/427; 424/437
[58] Field of Search ........................ 424/437, 427–428

[56] References Cited

U.S. PATENT DOCUMENTS

| 3,826,258 | 7/1974 | Abraham . |
| 3,845,201 | 10/1974 | Haddad et al. . |
| 3,914,402 | 10/1975 | Shell . |
| 3,968,201 | 7/1976 | Ryde .................................... 428/437 |
| 4,001,388 | 1/1977 | Shell . |
| 4,115,544 | 9/1978 | Shell . |
| 4,164,559 | 8/1979 | Miyata et al. . |
| 4,179,497 | 12/1979 | Cohen et al. . |

OTHER PUBLICATIONS

"Collagen as a Biomaterial", Stenzel et al, pp. 233–253, 1974.
"Collagen as a Vehicle for Drug Delivery", Rubin et al., pp. 309–312, Aug./Sep., 1973.
"Principles of Polymer Chemistry", Flory, pp. 49–68.
"Flow of Gases Through Polyethylene", Michaels et al., *Journal of Polymer Science*, vol. L, pp. 413–439 (1961).
*Contact Lens Practice*, Robert B. Mandell (Charles C. Thomas, 1965), pp. 159–165.
"Cyanamid Research Develops World's First Synthetic Absorbable Suture", *Chemistry and Industry*, Jul. 11, 1970; p. 905.
*General Opthalomogy*, Vaugn et al., Eds., 11th Edition; Ch. 7 "Tears", Khalid F. Tabbara M.D., pp. 77–72.

*Primary Examiner*—Nancy A. Swisher
*Attorney, Agent, or Firm*—Barnes & Thornburg

[57] ABSTRACT

An artificial tear suspension system is provided which includes bioerodible mucin-type particles, lipid-type material and aqueous-type material. The bioerodible mucin-type particles are suspended in either the lipid-type material or the aqueous-type material or both. The system provides all of the components of the natural tear film layers, and thus when administered to the eye provides an effective tear film which mimics the natural tear film.

20 Claims, 1 Drawing Sheet

ARTIFICIAL TEAR SUSPENSION

BACKGROUND AND SUMMARY OF THE INVENTION

An artificial tear system is provided. The system can be used for various treatments including the treatment of dry eye syndrome, whenever lubrication of the eye is desirable or when the eyes are subjected to dry conditions.

Under normal conditions, ocular fluid forms a thin layer approximately 7-10 μm thick that covers the corneal and conjunctival epithelium. This ultra thin layer provides a smooth optical surface to the cornea by abolishing minute surface irregularities of its epithelium, wets the surface of the corneal and conjunctival epithelium, thereby preventing damage to the epithelial cells, and inhibits the growth of microorganisms on the conjunctiva in the cornea by mechanical flushing.

The tear film normally includes a three layer structure. The outermost layer is a lipid layer derived from the secretions of the meibomian glands and thought to retard evaporation of the aqueous layer. The middle aqueous layer is provided by the major and minor lacrimal glands, and contains water-soluble substances. The inner most mucinous layer is composed of glycoprotein mucin and overlies the corneal and conjunctival epithelial cells. The epithelial cell membranes are composed of lipoproteins and are thus generally hydrophobic. The mucin plays an important role in wetting the surface, as the aqueous solution alone cannot wet this surface. Thus, the mucin provides a hydrophilic surface for the aqueous tears to spread out on and the surface is wetted by a lowering of the tears' surface tension. Under normal conditions, mucin is provided by goblet cells of the conjunctiva and is also provided from the lacrimal gland.

When any of the tear film components is deficient, the tear film will break up, and dry spots will form on the corneal and the conjunctival epithelium. Deficiency of any of the three components (aqueous, mucin or lipid) may result in dryness of the eye. There are many forms of the disease known as keratoconjunctivitis sica. Those connected with rheumatoid arthritis or other connective tissue disease are referred to as Sjögren's syndrome. All of this background information is discussed in the chapter on tears by Tabbara in Vaughan et al., *General Ophthalmology*, 11th Ed. (1986), pp. 72-77.

It is known to provide a large, solid, artificial tear insert which is placed into the eye. An example of such an insert is sold under the trademark LACRISERT. This rod contains hydroxpropyl cellulose which is slowly released over a period of time in the ocular environment. It is also suggested in Chapter 7 of *General Ophthalmology* to also apply topical artificial tears to the eye once the inserts are in place.

Not only do these large inserts sometimes cause irritation or blurring of vision, the inserts provide but one material which mimics only one layer of the tear film. The hydroxypropyl cellulose provides the mucin-type material to the tear film. Further, this treatment is not provided in an easy to use suspension form which delivers all of the treatment simultaneously to the eye. The insert must be placed in the eye using special techniques and then artificial tears could be added. The *General Ophthalmology* book does not discuss the actual composition of the artificial tears which may be added once the solid insert is in place.

As dry eye syndrome can be caused by deficiency of any of the three tear film components, the LACRISERT system does not provide a complete treatment for all cases of dry eye syndrome as all three components of the tear film layers are not present in the LACRISERT system.

It is thus an object of the present invention to provide an artificial tear treatment system which provides all components of the tear film layers. It is a further object to provide a treatment system to treat dryness of the eye successfully by providing all components which will form a tear film mimicking the natural tear film when administered to the eye. Thus, an object is to provide an artificial tear system which compensates for the deficiency of any or all of the natural tear film components, namely aqueous, mucin or lipid.

It is a further object to provide an artificial tear system which can be used any time lubrication is required for the eye or any time the eye is subjected to dryness. Thus, it is an object to provide an artificial tear system which can be used as ophthalmic lubricants, contact lens solutions, gonioscopic lens solutions, and other artificial tear systems.

Further objects include providing an artificial tear system which is easy to administer and which provides an effective delivery of the three components of the tear film.

These objects and other objects are achieved by providing an artificial tear suspension system. The system includes bioerodible mucin-type particles which release mucin-type material when placed in an ocular environment. Lipid-type material is provided which releases lipid-type material when placed in the ocular environment. Further, aqueous-type material is provided which releases aqueous-type material when placed in the ocular environment. The mucin-type particles are suspended in either the lipid-type material or the aqueous-type material or both.

The present invention provides an easy to administer system with effective delivery of all three of the components of the tear film layers. Once administered to the eye, the present invention three component system provides a tear film which perfectly mimics the natural tear film. Further, if natural production of any of the three components of the tear film is deficient, the present system compensates therefore, and thus is a very effective treatment of dryness of the eye, regardless of the cause.

Other objects, advantages and novel features of the present invention will become apparent from the following detailed description of the invention when considered in conjunction with the accompanying drawings.

DETAILED DESCRIPTION OF THE DRAWINGS

Figure 1:
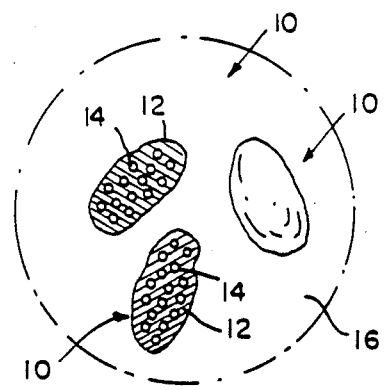
FIG. 1 is a magnified view of the particles of bioerodible material according to certain embodiments of the present invention.

In its simplest form, the present eye treatment system includes bioerodible mucin-type material particles, a lipid-type material and an aqueous-type material. The particles are suspended in the lipid-type material or the aqueous-type material which serves as a carrier. Thus, the material of all three layers is provided in one easy to administer suspension.

It is contemplated that in certain particularly preferred embodiments, the particles of bioerodible material also include various other components of natural tears in addition to or without components of the natural tear film layers as discussed above. The additional tear component material is either dispersed throughout the bioerodible particle, is encapsulated by the bioerodible material, or is included in the liquid or ointment carrier. Thus, according to certain preferred embodiments, other materials which can be included in the artificial tear bioerodible particles are glycoprotein mucin, lipoproteins, proteins such as albumen, globulins and lysozyme glucose, tear urea and other components such as those which assure a proper pH for the ocular environment.

According to other advantageous embodiments, topical solutions which have been used in eye drop form as artificial tears can be encapsulated in the bioerodible particle such that as the outer coating erodes, the artificial tears can be released to the eye over a period of time.

If a liquid carrier is utilized in the present suspension system, it may be an aqueous or non-aqueous ophthalmically acceptable sterile liquid.

Suitable non-aqueous liquid media include the physiologically acceptable oils such as silicon oil, USP mineral oil, white oil, and vegetable oils, for example, corn oil, peanut oil or the like. These oils provide lipid-type material for the treatment system.

To achieve a uniform dispersion of the particles in the liquid, the density of the liquid medium can be chosen such that it is equal to the density of the particles. Therefore, the particles will not float to the top of the liquid or sink to the bottom. If the liquid medium does not have the same density of the particles, the viscosity of the liquid medium can be adjusted in order to provide a uniform dispersion, or the dispensing system can achieve a dispersion by shaking or proper mixing immediately before administration.

In certain embodiments, the eye treatment liquid medium contains a variety of other materials to adjust pH, render the medium isotonic, preserve the treatment system and the like. Preservative agents which can be used include benzalkonium chloride in a concentration range of from 1:15,000 to 1:30,000; chlorobutanol in a concentration range of from 0.3% to 0.8%; thimerosol in a concentration range of from 0.001% to 0.003%; and phenyl mercuric nitrate in a concentration range of from 1:60,000 to 1:80,000. Also, in certain preferred embodiments, unpreserved unit or daily dose systems can be used. Other agents may be added to increase viscosity, promote suspension and/or improve ocular compatibility, such as methyl cellulose in an amount of from 0.1% to 0.7% or poly (vinyl alcohol) in an amount of from 0.4% to 2%. These and other additive materials are known in the art. A variety of these materials is generally described in the book *Contact Lens Practice,*. Robert B. Mandell (Charles C. Thomas, 1965) at pp. 159–165, which description is herein incorporated by reference.

In certain preferred embodiments, instead of using a liquid medium for the suspension, the particles can be suspended in an ointment such as lanolin, petrolatum and other known ointments. Most of these ointments provide lipid-type material to the treatment system.

The mucin-type material particles suspended in the liquid or ointment medium should be made of material which is bioerodible such that removal of the particles from the eye is not required as they are broken down and absorbed in the ocular environment (or resorbed). The term "bioerodible" is defined as a material which innocuously disintegrates or breaks down from a unit structure or enclosure over a prolonged period of time in response to the environment of the eye by one or more physical or chemical degradative processes, for example, enzymatic action, hydrolysis, ion exchange, dissolution by solubilization, emulsion formation or micelle formation. The bioerosion of the particles not only prevents a build-up of particles in the tissues of the ocular cavity, but also provides prolonged treatment of the eye which can be controlled such that the treatment is predictable.

Bioerodible materials used in the mucin-type material particles of the present suspension of this invention should be non-toxic. In certain preferred embodiments, the bioerodible materials should be capable of absorbing aqueous material in which they are soaked, and in certain other preferred embodiments, the bioerodible materials should be capable of forming films which wholly surround and enclose aqueous material to be delivered to the eye.

The mucin-type material should mimic the mucin component layer of the tear film. Thus, the material should act to hold aqueous material on the corneal and conjunctival epithelial cells. As discussed above, the epithelial cell membranes are composed of lipoproteins and are therefore relatively hydrophobic, and thus the surface cannot be wetted with an aqueous solution alone. Mucin plays the important role of wetting the surface. The mucin is partly adsorbed onto the corneal epithelial cell membranes and is anchored by the microvili of the surface epithelial cells. This provides a new hydrophilic surface for the aqueous tears to spread on, and the surface is wetted by a lowering of the tears' surface tension.

Thus, the mucin-type material provided in the present system should hold aqueous material to the surface of the epithelial cells. This aqueous material can be the natural tear fluid or the aqueous material provided in the present system. Thus, the mucin-type material particles bind aqueous material on the eye much like the natural mucin component of the tear film.

As will be discussed below, the mucin-type material particles can be hydrated prior to administration, and thus will be soft and malleable, providing comfort to the eye. Further, the water included in the hydrated particles will be delivered as an aqueous component of the tear film once administered to the eye.

It is desirable that the particles be comfortable when they are under the eyelids, as well as when they are on the surface of the eye in between the eyelids in the interpalpebral area, for example. In certain preferred embodiments, the particles are soft to help assure this comfort.

There are several naturally occurring materials, as well as synthetic materials, which are biodegradable and suitable for the mucin-type material of the present invention.

Examples of synthetic polymers that can be prepared which are biodegradable and provide mucin-type material for the treatment system include polylactides and polyglycolic acid. These biodegradable polymers are broken down into innocuous products such at carbon dioxide and water and they are also commercially available.

Useful polylactides includes both homopolymers and copolymers. Usually, these polylactides are prepared from the cyclic esters of lactic acids. Both $L(+)$ and $D(-)$ forms of lactic acid may be used to prepare the polylactides as well as the optically inactive DL-lactic acid mixture or any desired mixtures of $D(-)$ and $L(+)$ lactic acids.

Lactide copolymers offer an important degree of flexibility in choosing the life of a polymer matrix since this can be controlled through the amount and type of comonomer used. Some illustrative examples of suitable comonomers include: glycolide, $\beta$-propiolactone, tetramethylglycolide, $\beta$-butyrolactone, gamma-butyrolactone, pivalolactone, and intermolecular cyclic esters of $\alpha$-hydroxybutyric acid, $\alpha$-hydroxyisobutyic acid, $\alpha$-hydroxyvaleric acid, $\alpha$-hydroxyisovaleric acid, $\alpha$-hydroxycaproic acid, $\alpha$(-hydroxy- $\alpha$-ethylbutyric acid, $\alpha$-hydroxyisocaproic acid, $\alpha$-hydroxy-$\beta$-methylvaleric acid, $\alpha$-hydroxyheptanoic acid, $\alpha$-hydroxyoctanoic acid, $\alpha$-hydroxydecanoic acid, $\alpha$-hydroxymyristic acid, $\alpha$-hydroxystearic acid, $\alpha$-hydroxylignocenic acid, and $\beta$-phenyllactic acid.

Methods of preparing polylactides are well documented in the patent literature. The following U.S. Patents, the teachings of which are hereby incorporated by reference, describe in detail suitable polylactides, their properties and their preparation: Dorough, 1,995,970; Schneider, 2,703,316; Salzberg, 2,758,987; Zeile, 2,951,828; Higgins, 2,676,945 and 2,683,136; Trehu, 3,531,561; British Patent Specifications Nos. 755,447; 799,291; 825,335; 901,037; 932,382; 1,048,088; 1,123,445; West German Patent Nos. 946,664; 975,191; 1,112,293; 1,152,258; 1,153,902; East German Patent No. 14,548; French Patent Nos. 1,425,333; 1,478,694; 1,512,182; Netherlands Patent No. 99,836; Netherlands Patent Applications No. 6,605,197; 6,605,292; Japanese Nos. 17,675 (1966); 7,796 (1967); 2,948 (1968); 15,789 (1969).

Polyglycolic acids have been found to possess excellent biodegradable properties. Polyglycolic acid is the homopolymer of glycolic acid (hydroxyacetic acid). In the conversion of glycolic acid to polyglycolic acid, glycolic acid is initially reacted with itself to form the cyclic ester glycolide, which in the presence of heat and a catalyst is converted to a high molecular weight linear-chain polymer. Polyglycolic acids and their properties are described in more detail in the following article, the teachings of which are hereby incorporated by reference: "Cyanamid Research Develops World's First Synthetic Absorbable Suture", *Chemistry and Industry*, July 11, 1970, page 905.

The molecular weights of polypeptides and polyglycolic acid are closely related to both the exudation of any encapsulated aqueous material and the biodegradation of the matrix. It has been found that high molecular weights, i.e., $Mw=90,000$ or higher result in polymer matrices which retain their structural integrity for longer periods of time, while lower molecular weights, i.e., $Mw=30,000$ or below, result in both slower exudation and shorter matrix lives.

A preferred mucin-type particle material is collagen such as that obtained from pig sclera or cow skin and cross-linked with ultraviolet, or other forms of collagen cross-linked either by ultraviolet or X-ray.

The chemistry of a molecular structure and biochemical properties of collagen have been well established. The use of collagen as a vehicle for drug delivery as a bio-material is well known. U.S. Pat. No. 1,464,559 to Miyata et al. lists several publications discussing the use of collagen in drug delivery. An example is "Annual Review of Biophysics and Bioengineering", Vol. 3, pp. 231-253, 1974, by Miyata et al. Another example is Rubin et al., *J. Clin. Pharmacol.*, Vol. 13 (8/9):309-312 (1973), "Collagen as a Vehicle for Drug Delivery". The present invention uses the bioerodible properties and material thereby released along.

Collagen is a major protein of connective tissue such as cornea, skin, etc., and can be solubilized and purified by the treatment with proteolytic enzymes (other than collagenase) such as pepsin. Solubilized collagen is telopeptides-poor, relatively inexpensive, not antigenic and useful as a biomedical material. Enzyme solubilized native collagen is soluble in acidic PH, and soluble at physiological pH and at body temperature.

Native collagen is insoluble at physiological pH and at body temperature. Thus, native collagen must be changed such that the collagen erodes in the ocular environment so that physical removal thereof is not required.

The U.S. Patent to Miyata et al. shows various forms of chemically modified collagen which is erodible in the eye under physiological pH and under normal body temperatures.

Another material which can be used for the particles of the present invention is gelatin which is obtained by the selective hydrolysis of collagen and includes a complex mixture of high molecular weight water soluble proteins.

As used herein, the term cross-linked gelatin means the reaction product of gelatin or a gelatin derivative with a cross-linking agent which is reactive with either the hydroxyl, carboxyl or amino functional groups of the gelatin molecule but is substantially unreactive with the peptide linkages of the gelatin molecule. The product of cross-linking reaction preferably has an average molecular weight of from 20 to 50,000 between cross-links, while higher values can also be employed. These reaction products bioerode in the environment of the eye over a prolonged period of time.

Cross-linked gelatin materials and their preparations are well known. The degree of gelatin cross-linking is dependent upon the processing conditions employed and markedly affects the gelatin's bioerodibility. Exemplary cross-linking agents are: aldehydes, such as monoaldehydes, e.g., $C_1-C_4$ aldehydes, dialdehydes, epoxides, para-benzene quinone, and aqueous peroxydisulfate.

Aldehydes and ketones, especially the 1 to 4 carbon aldehydes and ketones are preferred, with formaldehyde being a most preferred cross-linking agent.

Irradiation is another suitable method for cross-linking gelatin; see for example Y. Tomoda and M. Tsuda, *J. Poly Sci.*, 54,321 (1961).

The reactive hydroxyl, carboxyl and amino groups are respectively present in gelatin in the appropriate amounts of 100, 75 and 50 meq per 100 grams. These quantities may serve as a general guide in determining the amount of cross-linking agent to be used.

Cross-linked gelatin is relatively permeable to ocular fluid so that gelatin serves as a very effective mucin-type material which will effectively hold and bind water mimicking the natural mucin component of tear film.

Other materials which can be used for the particles include polymers of polyvinyl alcohol, methyl cellulose, carboxy methyl cellulose and hydroxypropy methylcellulose. Particles can also include methyl cellulose derivatives and can include a combination of the bioerodible materials discussed above. Further, the treatment system can include a variety of different types of particles having different components to thereby vary the rate of erosion.

Crystallinity also affects the exudation and biodegradability rates. The polymer matrices having higher degrees of crystallinity have slower exudation rates and slower biodegradability. It is known that the crystallinity has a marked effect on physical properties. See Flory, Paul J., *Principles of Polymer Chemistry*, 5th printing, 1966 at pp. 49 et seq. It has also been reported in the literature that gaseous diffusion through polymeric membranes is slower, in general, for those polymers having higher degrees of crystallinity. See Michaels, A. S. and Bixler, H. J., "Flow of Gases through Polyethylene and Rubbery Polymers," *J. Poly. Sci.*, Vol. 50, pp. 413–439 (1961).

A good amount of control over the biodegradibility and release of encapsulated aqueous material can be obtained by choosing appropriate molecular weights and degrees of crystallinity in the polymer matrix. For example, if a relatively long release duration is desired, a high molecular weight polymer formed from a pure optical isomer of lactic acid can be used for the matrix; on the other hand, if a rapid release rate is desirable over a short duration, a low molecular weight lactide copolymer having a lower degree of crystallinity can be synthesized for use as the polymer matrix. Those skilled in the art will know or be able to determine by routine experimentation many suitable combinations of molecular weights and degrees of crystallinities of polylactides or polyglycolic acid to accomplish a desired release rate and duration.

Using one or more of the above parameters, polymeric matrices can be designed which have a great variety of exudation rates and biodegradability. Matrices can be synthesized to have lives shorter than, equal to or longer than the period of effective artificial tear delivery. For the shorter matrix lives, aqueous material delivery will be accomplished by a combination of aqueous material exudation and matrix biodegradation; for the longer matrix lives, aqueous material delivery will be substantially dependent on only aqueous material exudation. The degree of flexibility thus offered in designing the system of this invention is of great significance.

Further, the particles of the present invention, according to certain preferred embodiments, should be soft and malleable such that pressure created by the eyelid and the eye will deform the particles. In certain preferred embodiments, the particles can actually be in a semi-solid form as long as the particles do not dissolve in the liquid or oil medium in which they are suspended before administration to the eye.

Preferred methods for forming semi-solid particles include hydrating substances such as gelatin, collagen or polymers immediately before insertion or placing soft hydrated solids in a mixture or ointment base that will not permit them to dehydrate. Not only does the hydration provide soft, malleable particles, but also the water incorporated into the particles during hydration is delivered in the system as at least part of the aqueous component. Once in the eye, the mucin-type material particles mimic the natural mucin and hold and bind the water to the eye. Thus, the hydrated particles provide aqueous material in addition to the aqueous material when water is used as the liquid carrier. Further, when hydrated particles are placed in a lipid-type ointment an or oil carrier, the ointment or oil forces the water to remain in the particles as the ointment or oil medium is hydrophobic. Thus, in ointment or oil medium, the present invention can provide the aqueous component of the tear film from the water incorporated into the hydrated particles.

Hydration is generally performed by exposure of the particles to an aqueous solution such that water is incorporated into the particles. The particles should remain hydrated when administered to the patient.

The bioerodible material particles can be hydrated by placing the material in an aqueous solution carrier as discussed above. The aqueous carriers will hydrate the particles, and if the particles are left in the carrier, dehydration will be prevented.

Also, the bioerodible material can be hydrated by placing it in an aqueous soaking solution. Dehydration is prevented by placing the drug soaked particles in an aqueous carrier or in an ointment carrier. When dispersed in the ointment, the water will be retained in the particles and dehydration will thus be prevented by the ointment carrier.

Other methods for making materials which can be used for the particles of the invention malleable in form are known.

Although plasticizers are not the most preferred means to provide soft, malleable particles, examples of plasticizers which can be used in the present invention are shown in U.S. Pat. No. 4,179,497 to Cohen et al which shows large bioerodible inserts. A requirement of any plasticizers used is that the material be completely soluable in the ocular environment. Examples of suitable plasticizers include water, polyethylene glycol, propylene glycol, glycerine, trimethylol, propane, di and tripropylene glycol, hydroxypropyl sucrose and the like. Plasticizers can be present in the particles in various ranges. Although not the most preferred method of providing softness and malleability when plasticizers are used, they should be used in the lowest concentration possible and not greater than 20%.

Cohen et al recites a method of plasticizing a solid insert product with water. As applied to the present invention, the particles are contacted with air, having a relative humidity of at least about 40% until the particles pick up at least about 5% water, thereby becoming softer and more pliable. In certain preferred embodiments, the relevant humidity of the air is from about 60% to about 99% and the contact is continued until the water is present in the particles in amounts of from about 10% to about 20%.

It is contemplated to use any bioerodible material which is non-toxic, has the desired encapsulation properties if required, has appropriate diffusion and erosion properties, and which mimics the mucin component of the tear film. The materials discussed above are examples of preferred embodiments, but should in no way limit the materials used for the particles of the present suspension.

The lipid-type material can be provided in particle form and/or in the form of a liquid or ointment carrier for the mucin-type material particles. The lipid-type material can include all of the known lipids such as phospholipids, glycolipids and cholesterol. Further, the lipid can be in the form of waxes, esters, licithin, fatty alcohols and fatty acids. Also, the lipid can be in the form of petrolatum, either as an ointment carrier or as suspended particle globules. The term "particle" as defined herein encompasses globules or semi-solid masses. When suspended in an aqueous carrier, the lipid can also be in the form of micelles, liposomes, a bilayer, a globule or any other form. Further, the carrier medium can be a two component medium including both lipid-type materials, such as oil, and aqueous material. Such a system should be well shaken immediately prior to administration to assure mixing of the two carrier components.

The function of the lipid layer of the tear film provides a smooth surface and is thought to retard evaporation of the aqueous layer. Any material which is nontoxic and achieves these purposes can be used as the lipid-type material.

When the lipid is placed in the ocular environment, it is broken down by enzymes in the ocular environment such as by hydrolization or is melted by the body temperature present in the ocular environment, for example. Thus, if the lipid-type material is in a particle or semi-solid particle form suspended in the carrier, the lipid particles will not dissolve, but when placed in the ocular environment, the lipid particles will dissolve and provide lipid material for the lipid layer of the tear film.

Thus, the artificial tear system according to the present invention provides equivalents of all three components of the natural tear film in an easy to administer suspension. There are several combinations of the form of each of the three components in the suspension system which are contemplated. The present invention should not be limited to any specific form or combination of forms. The carrier can provide the aqueous component and/or the lipid component. Similarly, particles of the present suspension can provide any combination of the mucin component, the lipid component and the aqueous component. According to other advantageous embodiments, the artificial tear particles can be suspended in an oily or other lipid vehicle medium.

There are several processes which can be used to form the mucin-type or lipid-type particles of the present invention.

One method includes using a liquid or a mixture of the bioerodible material which is poured onto a flat surface. The film created is then allowed to dry as the solvent evaporates. Once the film has dried, the individual particles can be cut using known methods. A variety of methods can be used to cut the film into individual particles. According to most embodiments, this cutting can be done by a preformed mold cutter having the proper dimensions.

The thickness of the particles can be controlled by preparing the proper fluid phase of the bioerodible material. As an example, a solution of gelatin, collagen or carboxy methyl cellulose, for example, can be dried and then cut to the specific shape and dimensions or allowed to dry in appropriate molds.

According to certain preferred embodiments, the liquid mixture of bioerodible material is poured into a shallow pan or half-mold to the desired thickness. In certain embodiments, the pan or mold can include markings around the sides to indicate the thickness poured. In this way, the proper thickness can be assured. Subsequent to drying the particles are then cut in the remaining two dimensions.

In certain embodiments the liquid phase of the bioerodible material is not hydrated (the solvent is not aqueous). Further, even if the liquid phase is hydrated during pouring, the film or mold-forms are subsequently dehydrated when dried. In certain embodiments, the film or cut particles should be subsequently hydrated by soaking in an aqueous solution. The hydrated film or particles will expand to a certain degree depending on the amount of water incorporated therein. Thus, when determining the thickness of the film of bioerodible material which is not hydrated, the expected increase of thickness due to hydration should be compensated for by pouring a thinner film. However, due to the hydration, the particles will be soft and malleable in form.

According to a separate application of the present invention, the specific dimensions of the bioerodible particles is chosen such that certain optimum treatment conditions are met. A system which provides these specific dimensions is the subject matter of a patent application filed on same date. In this unique system, the particles are formed with a greatest dimension of at least 0.5 mm and a smallest dimension of no more than about 0.4 mm to 0.7 mm in the ocular environment.

Due to the specific minimum size of the largest particle dimension, this unique embodiment provides optimum prevention of drainage through the punctum, and thus provides optimum prolonged delivery, as well as a predictable dosage that will remain in the eye. It should be noted that this specification is merely a minium, and it is contemplated that the largest dimension be 0.4 mm or even larger to maximize the amount of material delivered. At the same time, due to the specific size of the smallest particle dimension in the ocular environment, the treatment system will not be uncomfortable or irritate the eye.

Further, if the particles are soft and malleable such as when they are hydrated, the smallest dimension prior to administration to the eye can be increased above the preferred range. The soft material will be less irritating to the eye. Further, if placed between the eyelid and the eye, the particles will be compressed to the proper non-irritatable range by the pressure between the eyelid and the eye. Also, as the particles are soft, they should conform to the eye and be comfortable even when disposed between the upper and lower eyelids. Thus, the thickness of the poured film can be increased when the particles are to be separated and thus malleable.

In certain preferred embodiments, the preferred hydrated thickness (smallest dimension) is in the range of about 0.4 mm–0.75 mm. However, if malleable, especially if semi-solid in form, the smallest dimension can be up to 1 mm if administered to the eye between the eyelid and the eye where pressure will compress the particles to the proper thickness.

Pouring of the film is but one method of controlling the thickness. Other methods include pouring into molds of the proper dimension, and cutting dried masses of the material to the proper thickness. The method of forming the particular thickness should not be limited to the examples given above. Regardless of the method for forming the proper dimensions, the preferred ranges of dimensions for this particular embodiment are discussed below.

Although the exact dimensions vary according to the specific materials and degree of deformation associated therewith, according to certain preferred embodiments, hydrated particles that will be compressed should be cut such that the smallest dimension is no greater than 0.4 mm to 1 mm prior to administration to the eye, and should be compressed to the range of no more than 0.4 mm to 0.7 mm in the ocular environment.

The largest dimension of the particles in this specific embodiment should be at least 0.5 mm, and can be as large as 3 mm to 4 mm or even larger to maximize the amount of material delivered. The drainage system of the eye includes the punctum which is an opening or aperture on the radial aspect of both upper and lower eye lid margins (in the medial corner of the upper and lower eyelids). The punctum has an average diameter of 0.5 mm. The punctum provides an opening into the drainage ducts or the lacrimal canaliculi of the drainage system which provides drainage of material out of the eye area. Material leaves the canaliculi, and passes through the lacrimal sac and nasolacrimal duct. Thus, the largest dimension of the particles should be greater than the size of the punctum to hinder drainage of the particles out of the eye through the punctum. According to certain preferred embodiments, the largest dimension is generally 1 mm to 2 mm. In certain preferred embodiments the third dimension or width should be about 0.5 mm or greater which further helps prevent drainage of the particles through the punctum. This third dimension can be 3 mm to 4 mm or even larger in certain preferred embodiments.

The balance of the two dimensions as discussed above provides a system which will not drain from the eye area, and which will at the same time reduce the chance of injury or irritation to the eye even though the system includes particles large enough such that drainage through the punctum is prevented. Thus, prolonged, continuous treatment is provided without irritation of the eye and without need for meticulous application requiring special insertion devices. This description of certain embodiments having specific dimensions is but one contemplated size of the particles. Other embodiments contemplated include particles of smaller size and larger size than those specified in the unique embodiments discussed above.

The particles can have any shape, including but not limited to: spheres, hemispheres, flat discs of any polygonal configuration, rounded discs, egg-shaped particles, cylinders, rods, elongated spaghetti-like forms, elongated box-forms, elongated rectangular or ribbon-like forms, and others.

Once the particles 12 are formed, they are then suspended in the liquid or ointment medium 16 (shown in FIG. 1). The treatment system can include different types of particles having any or all three of the major tear film components. Further, the treatment system can include different types of bioerodible material in the particles such that a differentiated rate of erosion can be achieved, thus providing a time release system for continuous long-term release of material to the eye.

Although clearly not limited to the following range, approximately 5 to 10 particles should be included in each dose. However, this dose can change depending upon the treatment required for the specific patient, such as the severity of dryness of the eye, the size of the particles or for the specific conditions presented.

The particles in suspension can be included in a conventional eye dropper bottle which provides for simple self-administration. According to certain preferred embodiments, the particles are included in a single dose container. Thus, the entire dosage is included in a single container with a dispensing end which the patient opens, and then drops the suspension into the eye. Thus, proper dosage is assured. As discussed above, the density of the liquid medium or the viscosity of the liquid medium can be used to assure uniform dispersion of the particles in the liquid medium or uniform dispersion can be provided by shaking immediately preceding administration.

In certain preferred embodiments, particles are dispersed in a standard eye ointment vehicle. The ointment can then be administered to the eye using standard procedures, For example, the lower eyelid is lifted out while the patient is looking up, and the ointment is then applied in the conjunctival sac. The lids should be closed for about one minute to allow the ointment to melt. Also, tubes having suitable openings for proper administration can be used.

The following examples are offered by way of illustration only and should not be construed as limiting the scope of the present invention in any way.

EXAMPLE I

A. A suspension of cross-linked collagen particles is prepared as follows:

Nine grams of collagen are added slowly with stirring to 40 grams of buffer solution at 90° C. The buffer solution includes one liter of distilled water, 7.1 grams of disodium hydrogen phosphate and 6.9 grams of sodium dihydrogen phosphate monohydrate. The pH should be 6.8. Forty Ml of the phosphate buffer and 0.15 grams chlorobutanol are combined with the heating and stirring. Alternatively, the collagen can be added to the buffer solution after it is cooled to room temperature and the mixture is then heated to 90° C. until the solution is complete.

The mixture is stirred thoroughly for four minutes until the temperature falls to 40° C. and is then poured into a pan of polyvinylchloride to a thickness which will give a dry thickness in the range generally of about 0.4 mm to 0.7 mm. The resulting film is dried at room temperature for one day.

A solution of formaldehyde (1% by weight) is prepared by addition of 13.1 grams of 38 percent formaldehyde reagent to 487 grams phosphate buffer (pH 6.8). The collagen films are submerged in this buffered formaldehyde solution for 20 minutes at room temperature, quickly rinsed with water and soaked in ice water for 2 hours. The films are removed from the ice water and dried overnight.

The dried film is then cut into individual particles using a mold cutter. The mold cutter forms disc-shaped particles having a diameter of 1 mm, and a thickness of 0.4 mm which was the thickness of the dried film.

B. A liquid carrier medium made of sterile distilled water, 1%w. poly (vinyl alcohol) and 0.004% benzalkonium chloride is prepared.

Figure 2:
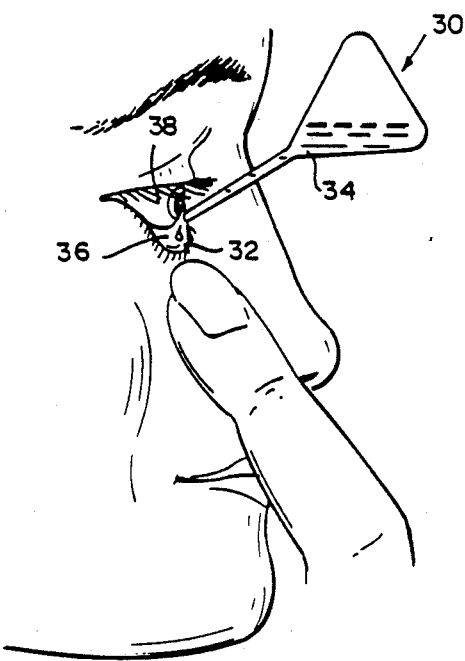
FIG. 2 is a pictorial view showing administration of the ophthalmic treatment system into the conjunctival sac of the eye.

A suspension of about 5 collagen particles per 0.25 cc of carrier medium is prepared. Also added to the carrier medium are about 5 globules of semi-solid petrolatum. These globules have three dimensions of about 0.5 mm by 1 mm by 1 mm. The drops of the suspension can be administered from a dispenser 30 by dropping the suspension into the eye. According to certain preferred embodiments, the lower eyelid 32 is pulled down and the suspension 34 is dropped into the area 36 between the eyelid 32 and the eye 38 as shown in FIG. 2. One administration containing from about 3 to 6 particles will provide continuous delivery of the tear film components for about 6 hours.

EXAMPLE II

The particles for an ointment suspension are prepared as described in Example IA. The particles are then placed in a liquid medium of sterile distilled water for 20 minutes. The particles will be hydrated and thus will incorporate the water therein.

The hydrated particles are then suspended in an ointment of petrolatum (40% solid petrolatum, 60% liquid petrolatum).

The ointment described above is administered to the patient using a tube with a wide dispenser opening.

EXAMPLE III

The treatment suspension is prepared as described in Example IA except rather than pouring the liquid bioerodible mixture on a sheet of polyvinyl chloride, the mixture is poured into a mold. The mold forms particles in the shape of hemispheres (half spheres) having a thickness of about 0.4 mm and a diameter of about 1 mm.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Artificial tear system comprising:
   bioerodible mucin-type particles for releasing mucin-type material when placed in an ocular environment to provide a hydrophilic surface to hold aqueous material in the ocular environment;
   lipid-type material for releasing lipid-type material when placed in the ocular environment to provide a layer to retard evaporation of aqueous material in the ocular environment;
   aqueous-type material for releasing aqueous-type material when placed in the ocular environment;
   wherein said mucin-type particles are suspended in at least one of said lipid-type material carrier and said aqueous-type material carrier.

2. A system as in claim 1, wherein said mucin-type particles are formed of at least one of collagen, gelatin and serum.

3. A system as in claim 1, wherein at least a portion of said lipid-type material is in the form of particles.

4. A system as in claim 3, wherein said lipid-type particles are formed of at least one of petrolatum, fatty acids, fatty esters, waxes, fatty alcohols and licithin.

5. A system as in claim 3, wherein said lipid-type particles are formed of at least one of glycoprotein, cholesterol and phospholipids.

6. A system as in claim 3, wherein said mucin-type particles are in a malleable form.

7. A system as in claim 3, wherein said mucin-type particles and said lipid-type particles have a largest dimension being at least 0.5 mm.

8. A system as in claim 3, wherein said mucin-type particles and said lipid-type particles have a greatest dimension of at least 0.5 mm and have a smallest dimension of no greater than about 0.4 mm to 0.7 mm when disposed in the ocular environment.

9. A system as in claim 3, wherein said mucin-type particles and said lipid-type particles are suspended in an aqueous-type material carrier medium.

10. A system as in claim 9, wherein a portion of said aqueous-type material is included in at least a portion of said bioerodible mucin-type particles.

11. A system as in claim 10, wherein said mucin-type particles and said lipid-type particles are suspended in a lipid-type material carrier medium.

12. A system as in claim 11, wherein said aqueous-type material is encapsulated in said at least a portion of bioerodible mucin-type particles.

13. A system as in claim 1, wherein at least a portion of said aqueous-type material is included in at least a portion of said bioerodible mucin-type particles.

14. A system as in claim 13, wherein said bioerodible mucin-type particles including aqueous-type material included therein are suspended in a lipid-type material carrier medium.

15. A system as in claim 14, further including an aqueous-type material carrier medium.

16. A system as in claim 1, wherein said bioerodible mucin-type particles are suspended in both a lipid-type material medium and an aqueous-type material medium.

17. A system as in claim 1, wherein at least a portion of said lipid-type material is incorporated in said mucin-type particles.

18. A system as in claim 1, wherein said mucin-type particles have a greatest dimension of at least 0.5 mm and have a smallest dimension of no greater than about 0.4 mm to 0.7 mm when disposed in the ocular environment.

19. A system as in claim 1, wherein said carrier is a fluid carrier in which said material and particles are suspended.

20. Method of treating the eye comprising:
    administering directly to the eye a suspension including:
    bioerodible mucin-type particles for releasing mucin-type material when placed in an ocular environment to provide a hydrophilic surface to hold aqueous material in the ocular environment;
    lipid-type material for releasing lipid-type material when placed in the ocular environment to provide a layer to retard evaporation of aqueous material in the ocular environment;
    aqueous-type material for releasing aqueous-type material when placed in the ocular environment;
    wherein said mucin-type particles are suspended in one of said lipid-type material and said aqueous-type material.

* * * * *